US005856591A

United States Patent [19]
MacKenzie et al.

[11] Patent Number: 5,856,591
[45] Date of Patent: *Jan. 5, 1999

[54] PROCESS FOR THE SEPARATION OF 2-ALKENE-1,4-DIOLS AND 3-ALKENE-1,2-DIOLS FROM CATALYSTS

[76] Inventors: Peter B. MacKenzie, 1040 Sussex Dr., Kingsport, Tenn. 37660; Jeffrey S. Kanel, 405 Pettyjohn Rd., Kingsport, Tenn. 37664; Stephen N. Falling, 522 Wakefield Ct., Kingsport, Tenn. 37663

Related U.S. Application Data

[60] Provisional application No. 60/022,117 Jul. 17, 1996.

[21] Appl. No.: 889,302
[22] Filed: Jul. 8, 1997
[51] Int. Cl.$^6$ .................................................... C07C 31/18
[52] U.S. Cl. ................................................................ 568/857
[58] Field of Search ...................... 568/852, 857, 568/868, 909.8

[56] References Cited

U.S. PATENT DOCUMENTS 5,530,167  6/1996  Tustin ..................................... 568/857

FOREIGN PATENT DOCUMENTS 54-73710  6/1979  Japan .
54-79214  6/1979  Japan .
57-2227   1/1982  Japan .

OTHER PUBLICATIONS

Ross et al., "Vinyl Epoxide Hydrolysis Reactions," *J. Am. Chem. Soc.,* vol. 102, pp. 1658–1665 (1982).
CA 101: 110030w (1984).
CA 96: 180770q (1982).
*10G–13 Heterocyclic Compounds,* 18462 (1960).
CA 91: 210877w (1979).
Compilation from SciFinder, pp. 1–6 and 1–4 (1997).
Derwent Abstracts, AN 95–099801.
Derwent Abstracts, AN 94–201497.
Derwent Abstracts, AN 95–099804.
Derwent Abstracts, AN 95–099803.
O. Fujimura, et al, Journal of Organic Chemistry, vol. 55, No. 6, 16 Mar. 1990, pp. 1705–1706.
M. Chini, et al., Tetrahedron, vol. 48, No. 18, 1 May 1992, pp. 3805–3812.

*Primary Examiner*—Michael L. Shippen
*Attorney, Agent, or Firm*—Burns, Doane, Swecker & Mathis, L.L.P.

[57] ABSTRACT

This invention pertains, firstly, to the use of mixtures of hydriodic acid and organic solvent soluble iodide salts as catalysts for the hydration of γ,δ-epoxyalkenes to form a mixture of the corresponding 2-alkene-1,4-diol and 3-alkene-1,2-diol isomers. Secondly, this invention describes the use of pH to control the 2-alkene-1,4-diol/3-alkene-1,2-diol product ratio, and achieve improved 2-alkene-1,4-diol selectivities by controlling the pH to near neutral values. Thirdly, this invention includes a catalyst recovery process whereby a liquid/liquid extraction is used to separate the product from the catalyst. In this extraction, γ,δ-epoxyalkene, or a γ,δ-epoxyalkene-containing organic solvent, is used to extract the catalysts from water, leaving the diol products in the aqueous phase, from which they may be subsequently recovered by distillation, extraction or by other means.

26 Claims, 2 Drawing Sheets

PROCESS FOR THE SEPARATION OF 2-ALKENE-1,4-DIOLS AND 3-ALKENE-1,2-DIOLS FROM CATALYSTS

This is a provisional application Ser. No. 60/022,177 filed Jul. 17, 1996.

FIELD OF THE INVENTION

This invention generally relates to a process for the preparation of mixtures of 2-alkene-1,4-diols (hereinafter "1,4-diol") and 3-alkene-1,2-diols (hereinafter "1,2-diol") from $\gamma,\delta$-epoxyalkenes. More particularly, the invention relates to a process for the hydrolysis of $\gamma,\delta$-epoxyalkenes to give a high 1,4-diol/1,2-diol ratio of these isomeric products wherein a mixture of $\gamma,\delta$-epoxyalkene and water is contacted with a catalytic mixture of an iodide salt and hydriodic acid under controlled pH conditions. The invention also relates to the use of an $\gamma,\delta$-epoxyalkene-containing organic solvent in a liquid/liquid extraction process to separate the catalyst components from the reaction products.

BACKGROUND OF THE INVENTION 1,4-Butanediol (BDO) is an important commodity chemical used in the manufacture of tetrahydrofuran, polyesters and polyurethanes. Most of the BDO produced commercially is made by the reaction of acetylene with two equivalents of formaldehyde followed by hydrogenation of the resulting alkyne. This process has various disadvantages including the use of relatively expensive and hazardous raw materials.

Some BDO is also produced by the reaction of acetic acid, oxygen, and 1,3-butadiene to produce 1,4-diacetoxy-2-butene which is then hydrogenated and hydrolyzed. This process suffers from various drawbacks including the number of steps involved and the coproduction of 3-butene-1,2-diol diacetate.

Other processes for producing BDO include the hydrogenation of maleic anhydride, and the hydroformylation of allyl alcohol followed by hydrogenation of the intermediate 4-hydroxybutyraldehyde. These processes also suffer from various drawbacks such as requiring severe operating conditions and requiring expensive rhodium catalyst, respectively.

An attractive route to BDO is through the hydrogenation of 2-butene-1,4-diol (hereinafter "1,4-butenediol"). However, there is no known way to synthesize 1,4-butenediol safely, efficiently, and inexpensively. It is known that 3,4-epoxy-1-butene (hereinafter "EPB") can be made efficiently from 1,3-butadiene and oxygen (see, e.g., U.S. Pat. Nos. 4,897,498 and 4,950,773), but there is no known process that can hydrolyze EPB to 1,4-butenediol with sufficiently high yield and selectivity.

For example, in *J. Am. Chem. Soc.,* 104, 1658–1665 (1982), Ross et al. teach that acid-catalyzed hydrolysis of EPB produces a mixture containing 96% 3-butene-1,2-diol (hereinafter "1,2-butenediol") and only 4% 1,4-butenediol. Likewise, we have found that hydrolysis of EPB with aqueous sodium hydroxide gives 1,2-butenediol, high boilers, and little or no 1,4-butenediol. Thus, neither acid nor base catalysis conditions are suitable for the hydrolysis of EPB to a product containing useful levels of the desired 1,4-butenediol isomer.

Japanese Kokai Patent No. 54-79214 describes a process that uses hydriodic acid and, optionally, a transition metal compound as a catalyst for the hydrolysis of EPB to mixtures containing 1,4-butenediol. Under the most selective conditions reported, the diol mixture had a 1,4/1,2 ratio of only 1.3 and a total diol yield of only 59%. Thus, this process not only gives a poor yield, but is also corrosive. Additionally, no method for the separation of the diol products from the catalyst components is disclosed.

Japanese Kokai Patent No. 54-73710 describes the use of both Cu(I) and Cu(II) salts as catalysts for the hydrolysis of EPB to mixtures of 1,4-butenediol and 1,2-butenediol. However, the reactions shown in the examples thereof were very slow and exhibited poor selectivity to the desired 1,4-isomer. For example, after 50 hours at elevated temperature, CuBr provided a mixture of diols having a 1,4/1,2 isomer ratio of only 0.34. Moreover, there is no disclosure of a process for separating and recovering the catalyst from the reaction product mixture.

U.S. Pat. No. 5,530,167 discloses a process for the hydrolysis of EPB to form a mixture of diols using a supported-copper catalyst. In an example thereof, it is reported that a NaY zeolite supported copper(II) catalyst gave a 1,4/1,2 ratio of 0.93.

Japanese Kokai Patent No. 57-2227 discloses a process for the hydrolysis of EPB to diols in the presence of an alkali metal iodide, alkaline-earth metal iodide, or zinc iodide and an acid selected from sulfuric acid, hydrochloric acid, hydrobromic acid, hydriodic acid, phosphoric acid and sulfonic acid. Under the best conditions reported, the 1,4/1,2 ratio was 5.15. Again, this process is highly corrosive and no method is disclosed for the separation of the products from the catalyst components.

Other known processes for the preparation of mixtures of 1,4-butenediol and 1,2-butenediol from EPB provide very low 1,4/1,2 ratios. For example, it is disclosed in DE 4429700 that EPB is hydrolyzed in the presence of rhenium oxide to give 3% 1,4-butenediol and 65% 1,2-butenediol (1,4/1,2 ratio=0.05). DE 4429699 discloses the hydrolysis of EPB in the presence of an insoluble oxide catalyst (e.g., 59% $SiO_2$, 38% $TiO_2$ and 0.25% F) to give 7% 1,4-butenediol and 54% 1,2-butenediol (1,4/1,2 ratio=0.13). And DE 4342030 discloses that non-catalyzed hydrolysis of EPB at 100° C. gave 100% conversion to a product containing 14% 1,4-butenediol and 71% 1,2-butenediol (1,4/1,2 ratio=0.20).

From the above, it can be seen that non-iodide processes for the hydrolysis of EPS give very low 1,4/1,2 ratios. While known iodide processes provide relatively higher 1,4/1,2 ratios, the ratio is still not high enough and its variability is not low enough for the hydrogenation of 1,4-butenediol to be an attactrive route to BDO. Moreover, such iodide processes are highly corrosive and, therefore, are not very attractive. Further, in the iodide processes, there is no disclosure of a method for separating the resulting products from the catalyst components. Thus, a need exists in the art for a process that can efficiently and selectively hydrolyze EPB to a product abundant in 1,4-butenediol with less corrosive effect. There is also a need in the art for a process for separating the resulting diol products from the catalyst components.

Accordingly, it is an object of the present invention to provide a process for the preparation of mixtures of 1,4-diol and 1,2-diol from $\gamma,\delta$-epoxyalkenes such as EPB having improved 1,4/1,2 selectivity and reduced variability.

It is a further object of the present invention to provide a process for the separation of catalyst components from the 1,4-diol and 1,2-diol product mixture.

These and other objects of the present invention will become apparent in light of the following specification, and the appended drawings and claims.

SUMMARY OF THE INVENTION

In a first aspect, the present invention relates to a process for the preparation of mixtures of 2-alkene-1,4-diols (hereinafter "1,4-diol") and 3-alkene-1,2-dials (hereinafter "1,2-diol") by reacting an γ,δ-epoxyalkene with water in the presence of an organic solvent soluble iodide salt and at least one of hydriodic acid, iodoalcohol, and precursors thereof.

In a second aspect, the present invention relates to a process for the preparation of mixtures of 1,4-diol and 1,2-diol from γ,δ-epoxyalkenes wherein the pH is controlled to obtained a desired selectivity of 1,4-diol/1,2-diol. The process includes the steps of:

(a) combining (i) an iodide salt with (ii) at least one of hydriodic acid, iodoalcohol, and precursors thereof and (iii) water to form an aqueous reaction mixture; and (b) adding γ,δ-epoxyalkene to the aqueous reaction mixture at a rate effective to maintain a substantially constant pH.

Preferably, the pH is maintained between about 5 and about 9 to maximize the selectivity of the 1,4-diol isomer. In an alternative embodiment, the pH is maintained at greater than about 9 or less than about 5 to increase the selectivity of the 1,2-diol isomer.

In a third aspect, the present invention relates to a process for the separation of mixtures of 1,4-diol and 1,2-diol from an aqueous mixture comprising (A) an iodide salt, (B) at least one of hydriodic acid, iodoalcohol, and precursors thereof, and (C) 1,4-diol and 1,2-diol. The process includes the step of contacting the aqueous mixture with an γ,δ-epoxyalkene-containing organic extraction solvent at conditions effective to convert the hydriodic acid, if present, to iodoalcohol and to form an aqueous phase comprising the 1,4-diol and 1,2-diol, and an organic phase comprising the iodoalcohol and iodide salt.

DETAILED DESCRIPTION OF THE INVENTION AND PREFERRED EMBODIMENTS

The first aspect of the present invention relates to a process for the preparation of mixtures of 1,4-diol and 1,2-diol by reacting an γ,δ-epoxyalkene with water in the presence of an organic solvent soluble iodide salt and at least one of hydriodic acid, iodoalcohol, and precursors thereof.

Various γ,δ-epoxyalkenes are suitable for the preparation of mixtures of 1,4-diol and 1,2-diol in the process of the present invention. Examples of such γ,δ-epoxyalkenes include, but are not limited to 3-methyl-3,4-epoxy-1-butene, 2-methyl-3,4-epoxy-1-butene, 2,3-dimethyl-3,4-epoxy-1-butene, 3,4-epoxy-1-butene, and the like. The preferred γ,δ-epoxyalkene is 3,4-epoxy-1-butene which produces a mixture of 2-butene-1,4-diol (hereinafter "1,4-butenediol") and 3-butene-1,2-diol (hereinafter "1,2-butenediol").

Sufficient amounts of water should be present to facilitate the hydrolysis of the γ,δ-epoxyalkene to obtain a mixture of the corresponding 1,4-diol and 1,2-diol. Preferably, from 2 to 100 parts by weight of water is used per 1 part by weight of the γ,δ-epoxyalkene.

By "organic solvent soluble iodide salt", we mean an iodide salt that is sufficiently soluble in an organic extraction solvent such that the iodide salt may be extracted from an aqueous phase containing the same into an organic phase containing the organic extraction solvent. Examples of such iodide salts and the organic extraction solvent are more fully discussed below in the second and third aspects of the invention.

By "iodoalcohol", we mean an isomeric adduct or a mixture of isomeric adducts formed from the reaction of hydriodic acid (HI) and the γ,δ-epoxyalkene. And by "precursors thereof", we mean a compound that is capable of reacting to form HI and/or iodoalcohol under reaction conditions without adversely affecting the desired chemistry. Such compounds are more fully discussed below in the second aspect of the invention.

Sufficient amounts of the catalyst components should be used in order to obtain a desired rate of reaction. The preferred amounts of the catalyst components are also more fully discussed below in the second aspect of the invention.

Preferably, the reaction is carried out at a temperature between 50° and 100° C., and a pressure of 1 to 10 bars.

For ease in understanding the remaining aspects of the invention, they will be described hereinafter with particular reference to the preferred starting compound of 3,4-epoxy-1-butene (hereinafter "EPB"). However, other γ,δ-epoxyalkenes can be used in the present invention to make mixtures of the corresponding 1,4-diol and 1,2-diol. Exemplary γ,δ-epoxyalkenes suitable for use in the present invention include, but are not limited to 3-methyl-3,4-epoxy-1-butene, 2-methyl-3,4-epoxy-1-butene, 2,3-dimethyl-3,4-epoxy-1-butene, and the like.

Figure 1:
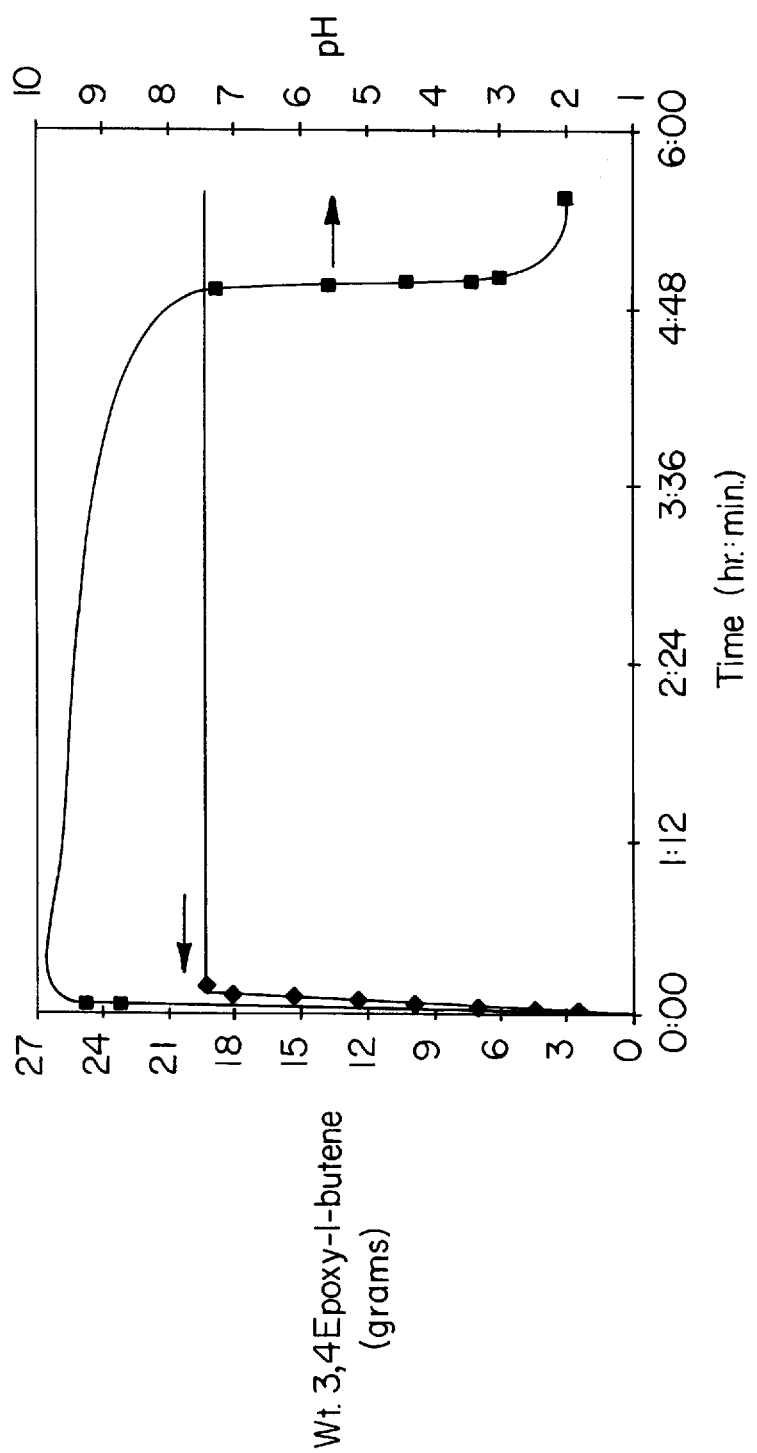
FIG. 1 is a graph of pH and weight of EPB versus time for the reaction of EPB with HI, MeBu$_3$NI, and water where the EPB is added all at once.

The second aspect of the invention is based, in part, on the surprising discovery that the pH of aqueous solutions of HI and an iodide salt is strongly dependent on the EPB concentration. That is, HI/iodide salt solutions which are initially strongly acidic (pH of about 1–2) can become strongly basic (pH of about 9–10 or higher) at sufficiently high EPB concentrations. For example, addition of 6.96 g of EPB to a mixture of 0.85 grams of 57% aqueous hydriodic acid, 66.48 grams of water, and 32.86 grams of methyltributylammonium iodide (MeBu$_3$NI) at 64° C. causes the pH to rise from 1.05 to 9.06. As the EPB is consumed, the pH falls, slowly at first, but then eventually dropping sharply, giving a pH versus time curve similar to that of an acid-base titration. See, e.g., FIG. 1. FIG. 1 will be discussed more fully below in Example 4.

Without wishing to be bound by theory, we attribute this result to the effects of reversible attack by iodide ion on EPE to generate a mixture of iodobutenols (4-iodo-2-buten-1-ol, 2-iodo-3-buten-1-ol, and/or 1-iodo-3-buten-2-ol) and hydroxide ion in aqueous solution. This reaction is shown in equation 1 below.

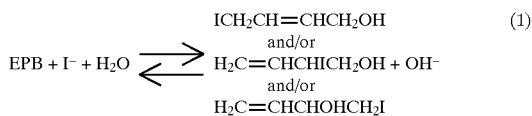

As the EPB concentration is increased, the equilibrium shifts to the right to generate more hydroxide and raise the pH. In the presence of dissolved iodide, the allylic iodobutenols are in equilibrium. This is shown in equation 2 below.

(2)

Reaction of the iodobutenols with water forms the butenediol products, liberates HI, and lowers the pH. This reaction is shown in equation 3 below.

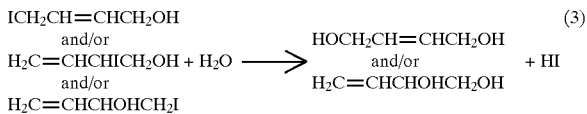

(3)

Depending on the pH, the reaction of the iodobutenols with hydroxide anion may also be important. In which case, iodide anion is the co-product, and the pH falls as hydroxide anion is consumed. In either case, if the concentration of EPB is controlled, the pH can be maintained at a substantially constant level. Alternatively, pH control may be achieved or assisted by the use of buffers as are familiar to those skilled in the art. Any buffer may be used in the present invention so long as it is substantially non-reactive with the γ,δ-epoxyalkene, products, and catalyst components.

By maintaining the pH at a desired level, the formation of either 1,4-butenediol or 1,2-butenediol can be maximized or increased. For instance, if the formation of 1,4-butenediol is to be maximized, then the pH should be maintained at a near neutral value, which minimizes 1,2-butenediol formation via acid or base catalyzed hydrolysis mechanisms. On the other hand, if the formation of 1,2-butenediol is to be increased, then the pH should be maintained at strong acidic or basic conditions.

Accordingly, in a particularly preferred embodiment, the process for the preparation of mixtures of 1,4-butenediol and 1,2-butenediol according to the second aspect of the present invention comprises the steps of:

(a) combining (i) an iodide salt with (ii) at least one of hydriodic acid, iodobutenol, and precursors thereof and (iii) water to form an aqueous reaction mixture; and (b) adding 3,4-epoxy-1-butene to the aqueous reaction mixture at a rate effective to maintain a substantially constant pH. By "substantially constant pH", we mean that the pH is maintained within the range which maximizes the production of either 1,4-butenediol or 1,2-butenediol.

When the yield of 1,4-butenediol is to be maximized, the reaction temperatures and pH should be such that the direct reaction of water with EPB is minimized relative to the iodobutenol-mediated reaction. In this case, temperatures of 50°–100° C. are preferred, with temperatures between 60° and 80° C. being most preferred, while pHs between about 5 and about 9 are preferred, with pHs between about 7 and about 8.5 being most preferred.

When more 1,2-butenediol is desired, the reaction conditions may be adjusted to increase the relative amount of 1,2-butenediol by lowering the catalyst concentration and/or raising the reaction temperature and/or adjusting the EPB concentration or added HI to give a higher or lower pH, e.g., greater than about 9 or less than about 5.

This process is preferably carried out at atmospheric pressure. However, it should be noted that the process can be operated at reduced or elevated pressure.

Without considering catalyst recovery, any iodide salt that is soluble in the aqueous reaction mixture at reaction conditions and that has a counter-ion that does not interfere with the desired chemistry can be used in the present invention. Examples of suitable iodide salts include compounds of the type $R^1R^2R^3R^4E^+I^-$, wherein $R^1$, $R^2$, $R^3$ and $R^4$ are groups containing only carbon and hydrogen, and E is nitrogen, phosphorous or arsenic, with tetraalkylammonium iodides being preferred. Metal iodides including, but not limited to alkali metal iodides and alkaline earth metal iodides, and crown ether complexes or podand complexes thereof may also be used. N-alkylpyridinium iodides, phosphazenium iodides, phosphazanium iodides, and cobaltacenium iodides are also included. HI salts of sterically hindered pyridines, including polymeric compounds, may also be used and may serve as a source of either the soluble iodide or HI or both. Examples of such sterically hindered pyridines include 2,6-dimethylpyridine, 2,4,6-trimethylpyridine, 2,6-di-tert-butylpyridine, 2,6-di-tert-butyl-4-methylpyridine, 2,4,6-tri-tert-butylpyridine, 2,6-diphenylpyridine, 2,4,6-triphenylpyridine, acridine, and 1,2,3,4,5,6,7,8-octahydroacridine. Of course, the sterically hindered pyridine used should be substantially non-reactive with the γ,δ-epoxyalkene, products, and catalyst components.

Enough iodide salt should be present to give an adequate reaction rate; iodide salt concentrations of about 0.25 to about 1N are preferred. If the catalyst is to be recovered by liquid-liquid extraction using EPB or an EPB-containing organic solvent, then the iodide salt should also have an extraction selectivity for the organic phase of greater than 1.

Either HI, iodobutenol, or precursors thereof or mixtures of those components can be used in combination with the iodide salt. By "iodobutenol", we mean an isomeric adduct or a mixture of isomeric adducts formed from the reaction of HI and EPB which includes 1-iodo-3-buten-2-ol, 2-iodo-3-buten-1-ol, and 4-iodo-2-buten-1-ol. By "precursors thereof", we mean a compound that is capable of reacting to form HI and/or iodobutenol under reaction conditions without adversely affecting the desired chemistry. Suitable precursors capable of reacting to form HI and/or iodobutenol include, but are not limited to iodine, organic iodides capable of liberating iodine, potassium triiodide and other triiodide salts, tertiary-butyl iodide, allyl iodide and other organic iodides subject to elimination or hydrolysis to liberate HI, collidinium hydroiodide and other adducts of HI with bases that are otherwise unreactive under the conditions of the process, zinc iodide, titanium tetraiodide and other metal iodides which can be hydrolyzed to release HI, mixtures of a strong acid (e.g., HCl, HBr, $H_2SO_4$, $H_3PO_4$ and other acids whose conjugate bases are otherwise unreactive under the conditions of the process) and an iodide salt, mixtures of iodide salts and any compound subject to hydrolysis to generate a strong acid.

Enough HI, iodobutenol, or precursor thereof should be used to give an adequate reaction rate. Initial concentrations of HI, iodobutenol, or precursor thereof between about 0.01 and about 0.25N are preferred.

It may be beneficial under certain circumstances to use a cosolvent in the present invention. The purpose of such optional cosolvents include solubilization of catalysts, γ,δ-epoxyalkene, and/or products in the reaction mixture. The cosolvent used should be substantially non-reactive with the γ,δ-epoxyalkene, products, and catalyst components. Examples of suitable cosolvents include acetone, acetonitrile, dioxane, tetrahydrofuran, 1-methyl-2-pyrrolidinone, N,N-dimethylformamide, and 2,5-dihydrofuran (hereinafter "DHF"). If substantial amounts of a cosolvent and/or solutes are used, then the preferred pH ranges mentioned herein may vary.

Experiments in which the pH is controlled in the 6–8 range give 1,4-diol/1,2-diol ratios in the range of about 5:1 to about 12:1. This range of selectivity represents a substantial improvement over previous, non-pH controlled approaches. Moreover, the near neutral pH conditions result in reaction mixtures which are less corrosive than the highly acidic mixtures of the prior art.

The conversion of HI to iodobutenol by reaction with EPB also forms the basis for a catalyst recovery scheme. If the aqueous product-containing feed is intimately contacted with pure EPB, or with an EPB-containing organic phase, then virtually all of the HI is converted into iodobutenol and extracted into the organic phase. If the iodide salt co-catalyst used has an extraction selectivity into the organic phase of greater than 1, then both the HI and the iodide salt catalysts can be efficiently separated from the highly water-soluble butenediol products via liquid-liquid extraction.

Accordingly, in a particularly preferred embodiment, the third aspect of the present invention relates to a process for separating mixtures of 1,4-butenediol and 1,2-butenediol from an aqueous mixture comprising (A) an iodide salt, (B) at least one of hydriodic acid, iodobutenol, and precursors thereof, and (C) 1,4-butenediol and 1,2-butenediol. The process includes the step of contacting the aqueous mixture with an EPB-containing organic extraction solvent at conditions effective to convert the HI, if present, to iodobutenol and to form an aqueous phase comprising the 1,4-butenediol and 1,2-butenediol, and an organic phase comprising the iodobutenol and iodide salt.

EPB may be used alone for extraction or in combination with a co-extraction solvent. At least some EPB is needed during extraction to ensure complete conversion of HI to the easily extractable iodobutenols and to avoid production of HI. Thus, the preferred extraction solvent is either EPB or a mixture of solvents that includes EPB.

The co-extraction solvent employed may be selected from a variety of organic solvents, depending on the chosen catalysts. Generally, the co-extraction solvent should satisfy four criteria: (1) it should form a separate liquid phase at equilibrium when contacted with the aqueous product-containing feed; (2) it should have a higher extraction selectivity for the iodobutenol and iodide salt catalysts than the butenediol products; (3) it should have characteristics that enable it to be recycled directly to the reactor and/or separated from the catalyst components by evaporation, distillation, crystallization, decantation, or some other separation operation; and (4) it should be substantially non-reactive with the EPB, products, and catalyst components.

Exemplary suitable co-extraction solvents include hydrocarbons (aliphatic and aromatic), haloaromatics, ketones, esters, ethers, amides, and mixtures thereof. Examples of hydrocarbon co-extraction solvents include: straight- and branched-chain alkanes containing from about 5 to 20 carbon atoms; aromatics such as benzene, toluene, and xylene; and straight- and branched-chain alkenes containing from about 5 to 20 carbon atoms. Examples of haloaromatics include: chlorobenzene, dichlorobenzene, and difluorobenzene. Examples of esters include: ethyl acetate, isopropyl acetate, n-propyl acetate, isobutyl acetate, and n-butyl acetate. Examples of ketones include: methyl ethyl ketone, methyl propyl ketone, methyl isobutyl ketone, methyl amyl ketone, diisobutyl ketone, and cyclohexanone. Examples of ethers include: diethyl ether, methyl t-butyl ether, and 2,5-dihydrofuran. Examples of amides include: 1-cyclohexyl-2-pyrrolidinone.

Alternatively, it is possible to use a dense gas as a co-extraction solvent for the catalyst species. Exemplary dense gases include, but are not limited to carbon dioxide, methane, ethane, propane, butane, isobutane, dimethyl ether, fluorocarbons, and mixtures thereof. The dense gas may contain one or more cosolvents to improve extractability of the iodide salts and iodoalcohols. Such cosolvents include, but are not limited to acetone, tetrahydrofuran, 1,4-dioxane, acetonitrile, and mixtures thereof.

In this aspect of the invention, the iodide salt co-catalyst should have solubility properties such that it can both dissolve in the aqueous reaction mixture and be later recovered in the organic phase used for the catalyst recovery. The iodide salt co-catalyst and the iodoalcohol should be selectively extracted into the organic phase with respect to the 1,2- and 1,4-diols. Thus, the quaternary ammonium, phosphonium, and arsonium iodides are preferred. Tetraalkylammonium iodides are most preferred for this purpose, with $MeBu_3NI$ being especially preferred.

In the case where the catalyst employed to prepare mixtures of 1,4-diol and 1,2-diol is an HI salt of a sterically hindered pyridine, the HI salt can be extracted from the aqueous product mixture without the use of a $\gamma,\delta$-epoxyalkene-containing extraction solvent. Such salts can simply be extracted with any of the aforementioned co-extraction solvents.

The separation process of this invention may be carried out in batch, semi-continuous, or continuous modes of operation. For example, batch operation may comprise charging the aqueous product-containing feed and the extraction solvent to a vessel, agitating the dispersion to effect mass transfer, and separating the two immiscible liquid phases. One of the resulting liquid phases comprise the extraction solvent containing the iodobutenol and iodide salt. We prefer the use of EPB as the extraction solvent since it can be recycled directly to the reactor without the need for separating the catalysts from the extraction solvent. The second liquid phase, which is aqueous and contains the butenediols, may be extracted repeatedly, as needed, to give the desired degree of catalyst recovery before the stream is treated to recover the butenediol products. These repeated extraction steps include contacting the aqueous phase with the extraction solvent in a crossflow, co-current, or countercurrent pattern.

The extraction process is preferably operated continuously or semi-continuously in a countercurrent manner. This technique, as well known in the art, can give excellent efficiencies of extraction. See, for example, T. C. Lo, M. H. I. Baird, C. Hanson, *Handbook of Solvent Extraction*, Reprint Edition, Krieger Publishing Company, Malabar, Fla., 1991. Typical countercurrent extraction equipment generally includes columns (agitated and non-agitated), mixer-settlers, and centrifugal extractors. Examples of agitated columns include: the Karr reciprocating plate, rotating disc, asymmetric disc, Kuhni, York-Scheibel, and the Oldshue-Rushton. Examples of non-agitated columns include: spray, baffle plate, packed, and perforated plate. Examples of centrifugal extractors include those produced by: Robatel Inc., Pittsfield, Mass.; Westfalia Separator Inc., Northvale, N.J.; and Baker Perkins Inc. (Podbielniak), Saginaw, Mich. In the continuous mode of operation, the aqueous product-containing feed and the extraction solvent are continuously charged to the extractor. The two immiscible phases are intimately contacted in the extractor where they flow countercurrently to one another. The hydrogen iodide, if present, is converted into iodobutenol and is extracted into the extracting solvent along with the iodide salt. The butenediol products remain in the aqueous phase as it passes through the extractor.

The batch, semi-continuous, or continuous extraction may be performed over a wide range of temperatures and pressures. However, the extraction temperature should remain above the point where a solid phase is generated by precipitation or crystallization. As a result, we prefer to operate the extractor between 10° and 100° C. with a pressure necessary to prevent evaporation of the solvents.

For dense gas extraction, we prefer to operate the extractor at a temperature between 10° and 150° C., and a pressure between about 1 and about 450 bar.

EXAMPLES

The present invention is further illustrated by the following examples. The structures of the products obtained were confirmed by nuclear magnetic resonance spectroscopy and mass spectrometry. All percentages reported below are based on weight unless otherwise indicated.

EXAMPLE 1

Hydrolysis of EPB

To a 100-mL, stainless steel, stirred autoclave equipped with a condenser, helium supply, back-pressure regulator, EPB feed line (fed from a reservoir by a pump), pH probe, heating mantle, and cooling coils was charged 30.4 g (0.093 mole) of MeBu$_3$NI, 48.0 g of deionized water, and 6.08 g (0.022 mole) of 47% hydriodic acid. The autoclave was sealed and pressurized to 25 psig with helium. The initial reaction mixture had a pH of about 2. Agitation was begun and the mixture heated to 65° C. EPB was pumped in quickly to bring the pH up to 7.8. Thereafter, EPB was pumped into the mixture automatically as needed to maintain a pH of 7.3–7.4. The temperature was controlled at 64°–66° C. A total of 20.5 g (0.292 mole) of EPB was added over a period of 363 minutes. A sample of the final mixture was analyzed by GC: 12.03% 1,4-butenediol, 1.59% 1,2-butenediol, 43.99% water, and 24.71% MeBu$_3$NI. The 1,4-butenediol/1,2-butenediol ratio was therefore 7.57:1.

Figure 2:
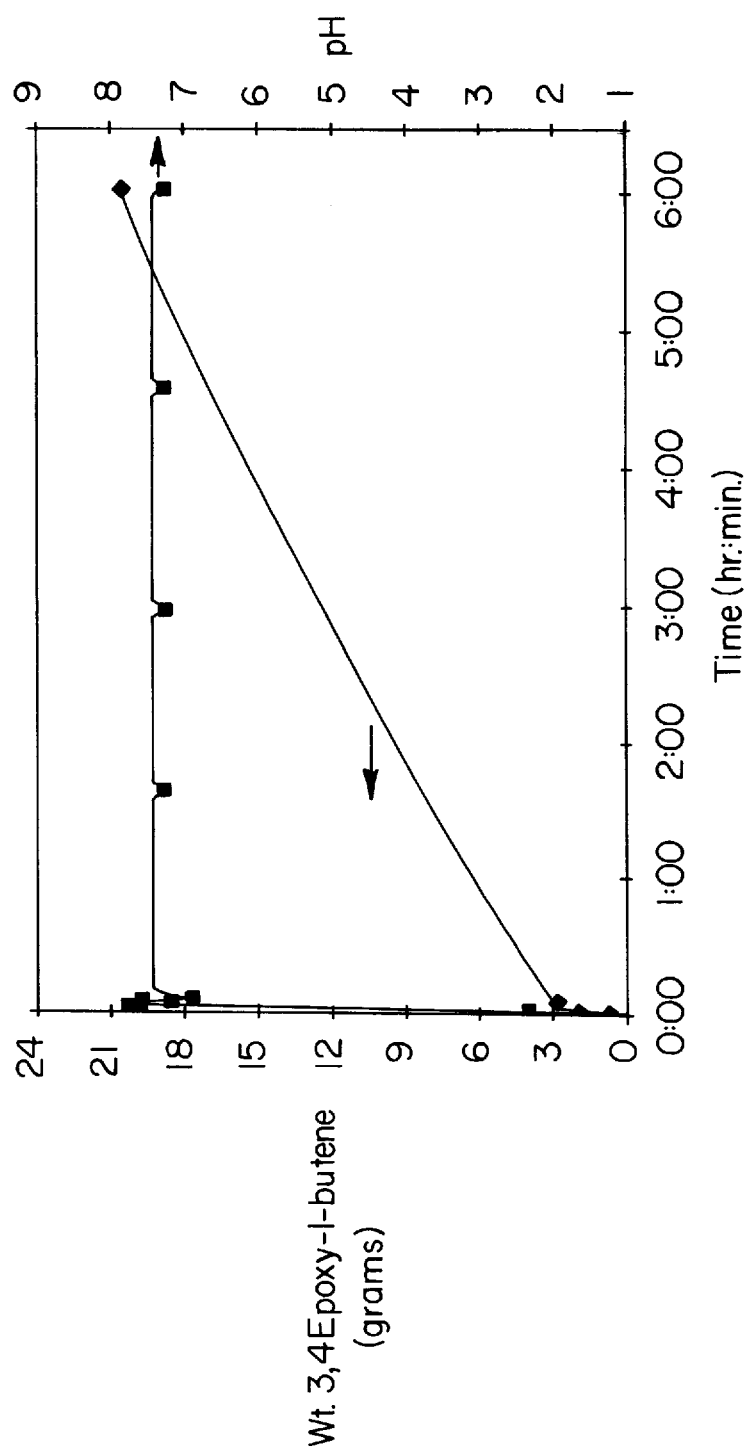
FIG. 2 is a graph of pH and weight of EPB versus time for the reaction of EPB with HI, MeBu$_3$NI, and water where the EPB is added at a rate such that the pH is maintained substantially constant.

The pH and the weight of EPB added as a function of time is graphically depicted in FIG. 2. As seen in FIG. 2, the pH remained substantially constant during the reaction as the amount of EPB added to the reaction mixture steadily increased.

EXAMPLE 2

Hydrolysis of EPB

To a 100-mL, stainless steel, stirred autoclave equipped with a condenser, helium supply, back-pressure regulator, EPB feed line (fed from a reservoir by a pump), pH probe, heating mantle, and cooling coils was charged 15.4 g (0.093 mole) of potassium iodide, 48.0 g of deionized water, and 6.08 g (0.022 mole) of 47% hydriodic acid. The autoclave was sealed and pressurized to 25 psig with helium. The initial reaction mixture had a pH of about 2. Agitation was begun and the mixture heated to 65° C. EPB was pumped in quickly to bring the pH up to 7.25. Thereafter, EPB was pumped into the mixture automatically as needed to maintain a pH of 7.25. The temperature was controlled at 64°–66° C. A total of 14.6 g (0.208 mole) of EPB was added over a period of 339 minutes. A sample of the final mixture was analyzed by GC: 11.27% 1,4-butenediol, 2.64% 1,2-butenediol, and 60.85% water. The 1,4-butenediol/1,2-butenediol ratio was therefore 4.27:1.

EXAMPLE 3

Hydrolysis of EPB

A five-liter, three-neck, round-bottom flask was equipped with a mechanical stirrer, pH electrode, condenser, heating mantle, and EPB addition tubing. The pH electrode was connected to a pH controller which controlled the EPB addition pump. To the flask was charged 669.3 g (2.045 moles) of MeBu$_3$NI, 1710 g (95 moles) of water, 30 g (0.11 moles) of 47% aqueous hydrogen iodide, and 138 g (1.53 moles) of 1,4-butanediol. The mixture had a pH of 1.05. EPB (14.0 g) was added slowly to this mixture at room temperature until the pH was 7.0. The orange mixture was then heated to 65° C. while controlling the pH at 7.4 to 7.5 by the automatic addition of EPB. After the solution reached 65° C., the color changed to light yellow and remained that color throughout the rest of the EPB addition. The EPB addition rate was about 31 g/min. After 11.5 hours, the heating was turned off and the reaction temperature allowed to fall (pH control was continued in order to maintain the pH at 7.4 to 7.5). A total of 376.4 g (5.370 moles) of EPB was added. The GC assay of the final mixture was 0.20% EPB, 56.2% water, 19.1% MeBu$_3$NI, 1.5% 3-butene-1,2-diol, 9.3% 2-butene-1,4-diol, and 3.4% 1,4-butanediol. The ratio of 1,4-butenediol/1,2-butenediol was therefore 6.05:1.

EXAMPLE 4

Hydrolysis of EPB

To a 100-mL, stainless steel, stirred autoclave equipped with a condenser, helium supply, back-pressure regulator, EPB feed line (fed from a reservoir by a pump), pH probe, heating mantle, and cooling coils was charged 30.4 g (0.093 mole) of MeBu$_3$NI, 48.0 g of deionized water, and 6.08 g (0.022 mole) of 47% hydriodic acid. The autoclave was sealed and pressurized to 25 psig with helium. The initial reaction mixture had a pH of about 2. Agitation was begun and the mixture heated to 65° C. To the mixture was quickly added (over 7 minutes) 19.3 g (0.28 mole) of EPB giving a pH of 9.7. Thereafter, the temperature was controlled at 64°–66° C. and the pH was allowed to drift. A sample of the mixture after 62 minutes (pH 9.5) was analyzed by GC: 0.91% 1,4-butenediol, 0.83% 1,2-butenediol, 49.0% water, and 21.9% MeBu$_3$NI. The 1,4-butenediol/1,2-butenediol ratio was therefore 1.10:1.

After 5.5 hours, the pH had gone to 1.9. A sample of the final mixture was analyzed by GC: 8.73% 1,4-butenediol, 2.12% 1,2-butenediol, 46.75% water, and 22.2% MeBu$_3$NI. The 1,4-diol/1,2-diol ratio was therefore 4.12:1.

The pH and the weight of EPB added as a function of time is graphically depicted in FIG. 1. As seen in FIG. 1, the pH fluctuated over the course of the reaction since the EPB was added all at once.

EXAMPLE 5

Hydrolysis of EPB

To a 100-mL, stainless steel, stirred autoclave equipped with a condenser, helium supply, back-pressure regulator, EPB feed line (fed from a reservoir by a pump), pH probe, heating mantle, and cooling coils was charged 15.4 g (0.0928 mole) of KI, 48.0 g of deionized water, and 3.80 g (0.0056 mole) of zinc iodide. The autoclave was sealed and pressurized to 14 psig with helium. The initial reaction mixture had a pH of about 6.8. Agitation was begun and the mixture heated to 65° C. EPB was pumped into the mixture automatically as needed to maintain a pH of 7.3–7.4. The temperature was controlled at 64°–66° C. A total of 16.9 g (0.241 mole) of EPB was added over a period of 559 minutes. A sample of the final mixture was analyzed by GC: 14.3% 1,4-butenediol and 2.64% 1,2-butenediol. The 1,4-butenediol/1,2-butenediol ratio was therefore 5.42:1.

EXAMPLE 6

Hydrolysis of EPB

To a 100-mL, stainless steel, stirred autoclave equipped with a condenser, helium supply, back-pressure regulator, EPB feed line (fed from a reservoir by a pump), pH probe, heating mantle, and cooling coils was charged 20.2 g (0.0927 mole) of tetramethylphosphonium iodide, 48.0 g of deionized water, and 6.08 g (0.0223 mole) of 47% hydriodic acid. The autoclave was sealed and pressurized to 14 psig with helium. The initial reaction mixture had a pH of about 1.5. Agitation was begun and the mixture heated to 65° C. EPB was pumped in quickly to bring the pH up to about 8. Thereafter, EPB was pumped into the mixture automatically as needed to maintain a pH of 7.3–7.4. The temperature was controlled at 64°–66° C. A total of 19.5 g (0.278 mole) of EPB was added over a period of 376 minutes. A sample of the final mixture was analyzed by GC: 9.89% 1,4-butenediol and 2.24% 1,2-butenediol. The 1,4-butenediol/1,2-butenediol ratio was therefore 4.42:1.

EXAMPLE 7

Hydrolysis of EPB

To a 100-mL, stainless steel, stirred autoclave equipped with a condenser, helium supply, back-pressure regulator, EPB feed line (fed from a reservoir by a pump), pH probe, heating mantle, and cooling coils was charged 30.4 g (0.0929 mole) of MeBu$_3$NI, 48.1 g of deionized water, and 3.03 g (0.0111 mole) of 47% hydriodic acid. The autoclave was sealed and pressurized to 14 psig with helium. The initial reaction mixture had a pH of about 2.6. Agitation was begun and EPB was pumped in at room temperature to quickly bring the pH up to about 8. The mixture was heated to and held at 64°–65° C. while pumping in EPB automatically as needed to maintain a pH of 7.3–7.4. A total of 15.9 g (0.229 mole) of EPB was added over a period of 656 minutes. A sample of the final mixture was analyzed by GC: 50.68% water, 0.13% EPB, 0.49% DHF, 0.29% crotonaldehyde, 28.3% MeBu$_3$NI, 11.53% 1,4-butenediol, and 1.35% 1,2-butenediol. The 1,4-butenediol/1,2-butenediol ratio was therefore 8.54:1.

EXAMPLE 8

Hydrolysis of EPB

To a 100-mL, stainless steel, stirred autoclave equipped with a condenser, helium supply, back-pressure regulator, EPB feed line (fed from a reservoir by a pump), pH probe, heating mantle, and cooling coils was charged 30.4 g (0.0929 mole) of MeBu$_3$NI, 48.0 g of deionized water, and 6.08 g (0.0223 mole) of 47% hydriodic acid. The autoclave was sealed and pressurized to 14 psig with helium. The initial reaction mixture had a pH of about 1.7. Agitation was begun and the mixture heated to 65° C. EPB was pumped into the mixture automatically as needed to maintain a pH of 2.0. The temperature was controlled at 64°–66° C. A total of 15.3 g (0.218 mole) of EPB was added over a period of 295 minutes. A sample of the final mixture was analyzed by GC: 8.89% 1,4-butenediol and 3.88% 1,2-butenediol. The 1,4-butenediol/1,2-butenediol ratio was therefore 2.29:1.

EXAMPLE 9

Hydrolysis of EPB

To a 100-mL, stainless steel, stirred autoclave equipped with a condenser, helium supply, back-pressure regulator, EPB feed line (fed from a reservoir by a pump), pH probe, heating mantle, and cooling coils was charged 0.60 g (0.0056 mole) of 2,6-dimethylpyridine, 48.0 g of deionized water, and 1.52 g (0.00559 mole) of 47% hydriodic acid. The autoclave was sealed and pressurized to 14 psig with helium. The initial reaction mixture had a pH of about 3.4. Agitation was begun and the mixture heated to 65° C. EPB was pumped into the mixture automatically as needed to maintain a pH of 7.4. The temperature was controlled at 64°–66° C. A total of 11.4 g (0.163 mole) of EPB was added over a period of 21.4 hours. A sample of the final mixture was analyzed by GC: 10.3% 1,4-butenediol and 0.90% 1,2-butenediol. The 1,4-butenediol/1,2-butenediol ratio was therefore 11.4:1.

This example shows that an HI salt of a sterically hindered pyridine can be used as a source of HI. It also shows the beneficial effect of a sterically hindered pyridine as a buffering agent.

EXAMPLE 10

Hydrolysis of EPB

To a 100-mL, stainless steel, stirred autoclave equipped with a condenser, helium supply, back-pressure regulator, EPB feed line (fed from a reservoir by a pump), pH probe, heating mantle, and cooling coils was charged 14.3 g (0.0928 mole) of tetramethylammonium bromide, 48.0 g of deionized water, and 1.9 g (0.011 mole) of 48% hydrobromic acid. The autoclave was sealed and pressurized to 14 psig with helium. The initial reaction mixture had a pH of about 1.6. Agitation was begun and the mixture heated to 65° C. EPB was pumped in quickly to bring the pH up to about 8. Thereafter EPB was pumped into the mixture automatically as needed to maintain a pH of 7.3–7.4. The temperature was controlled at 64°–66° C. A total of 16.5 g (0.235 mole) of EPB was added over a period of 363 minutes. A sample of the final mixture was analyzed by GC: 8.95% 1,4-butenediol and 6.7% 1,2-butenediol. The 1,4-butenediol/1,2-butenediol ratio was therefore 1.34:1.

Comparative Example 1

Hydrolysis of EPB Using Sulfuric Acid Alone

A five-liter, three-neck, round-bottomed flask was set up with a heating mantle, condenser, thermometer, mechanical stirrer, and addition funnel. To the flask was charged 3000 mL of deionized water and 0.4 mL of concentrated sulfuric acid. The pH of the solution was 2. The solution was heated to 55° C. then 521.0 g (7.433 mole) of 99.6% EPB was added dropwise over 90 minutes from the addition funnel. The temperature was allowed to rise to 77°–85° C. during the addition. The rate of addition was such that the mixture remained homogeneous. After addition, the mixture was refluxed for one hour. GC showed no unreacted EPB, 10% 1,4-butenediol, 85.5% 1,2-butenediol, and 4.5% high boilers. The ratio of 1,4-butenediol/1,2-butenediol was therefore 0.12:1.

Comparative Example 2

Hydrolysis of EPB Using Hydriodic Acid Alone

A 500-mL, four-neck, round-bottomed flask was set up with a heating mantle, condenser, thermocouple, magnetic stirrer, and addition funnel. To the flask was charged 200 mL of deionized water and 4 mL (0.047 mole) of 47% hydriodic acid. The pH of the solution was 1. The solution was heated to 60° C. then 21.6 g (0.308 mole) of EPB was added dropwise over 53 minutes from the addition funnel. The temperature was held at 60°–65° C. during the addition. The rate of addition was such that the mixture remained homogeneous. After addition the mixture was refluxed for one hour. GC showed no unreacted EPB, 1.72% 1,4-butenediol, and 6.99% 1,2-butenediol. The ratio of 1,4-butenediol/1,2-butenediol was therefore 0.25:1.

EXAMPLE 11

Determination of Distribution Coefficients of Various Onium Halides

Distribution coefficients quantify how solutes, compounds to be transferred across a liquid-liquid interface, will distribute between two immiscible liquid phases at equilibrium. Typically, in liquid extraction a feed that contains one or more solutes is intimately contacted with a solvent, and two liquid phases result. The solute(s) transfer from the feed phase into the solvent phase. The feed depleted in the solute(s) is termed the raffinate, and the solvent phase, which has gained solute(s), is called the extract. The distribution coefficients are defined as the concentration of a solute in the extract divided by the concentration of the solute in the raffinate, and it does not need to be greater than unity for the extraction to be feasible. However, larger values of the distribution coefficient are preferred, as that reduces the solvent requirements and/or the number of countercurrent stages required for the extraction. The extraction selectivity refers to the ability of a solvent to extract one compound in a solution preferentially over another, and it is computed by dividing the distribution coefficient of the solute by the distribution coefficient of the other component of interest.

Thus, the most desirable solvent would extract a maximum amount of one component and a minimum amount of the other. The extraction selectivity is analogous to the relative volatility for distillation processes. Therefore, its value must not equal unity for the separation to be feasible.

The distribution coefficients and extraction selectivities were experimentally measured for many onium halide systems including tetramethyl phosphonium iodide ($Me_4PI$), trimethyl phenyl phosphonium iodide ($Me_3PhPI$), dimethyl diphenyl phosphonium iodide ($Me_2Ph_2PI$), methyl triphenyl phosphonium iodide ($MePh_3PI$), tetrabutyl phosphonium iodide ($Bu_4PI$), tetramethylammonium iodide ($Me_4NI$), tetraethylammonium iodide ($Et_4NI$), tetrabutylammonium iodide ($Bu_4NI$), tetrahexylammonium iodide ($Hex_4NI$), methyl tributylammonium iodide ($MeBu_3NI$), phenyltributylammonium iodide ($PhBu_3NI$), tetrabutylphosphonium bromide ($Bu_4PBr$), and tetraethylammonium bromide ($Et_4NBr$). Approximately two grams of demineralized water, two grams of solvent, and 0.5 grams of onium halide were added to a graduated glass centrifuge tube. The solvent used was EPB, 2,5-dihydrofuran (hereinafter "DHF"), or mixtures thereof. The dispersion was intimately contacted by vortex mixing for five minutes before it was centrifuged at 2300 times the gravitational force for ten minutes. Samples of each phase were taken and analyzed by Proton Nuclear Magnetic Resonance Spectroscopy, and the concentration of water, solvent, and the onium halide were determined. The distribution coefficient of the onium halide between the organic- and aqueous-rich phases was computed. The extraction selectivity of the solvent for the onium halide with respect to water was then calculated. The results are shown in Table 1.

TABLE 1

Phase equilibrium data for the onium halide, water and EPB system as a function of temperature.

| Temp. (°C.) | Catalyst | Organic Phase | Catalyst Charged (g) | Organic Charged (g) | Water Charged (g) | Organic Phase | | | |
|---|---|---|---|---|---|---|---|---|---|
| | | | | | | EPB by diff. (wt %) | DHF by diff. (wt %) | Water (wt %) | Cat. (wt %) |
| 25 | $Me_4PI$ | EPB | 0.4260 | 1.8425 | 1.8496 | 94.9 | 0.0 | 5.1 | 0.0 |
| 25 | $Me_3PhPI$ | EPB | 0.4089 | 1.9024 | 2.6700 | 94.7 | 0.0 | 4.9 | 0.4 |
| 25 | $MePh_3Pt$ | EPB | 0.4717 | 1.8107 | 1.8458 | 71.6 | 0.0 | 10.5 | 18.0 |
| 25 | $Bu_4PI$ | EPB | 0.5310 | 1.8720 | 1.9182 | 71.6 | 0.0 | 8.1 | 20.3 |
| 25 | $Et_4NI$ | EPB | 0.4871 | 1.9681 | 1.9843 | 95.5 | 0.0 | 4.5 | 0.1 |
| 25 | $Bu_4NI$ | EPB | 0.4936 | 1.7849 | 2.0229 | 67.1 | 0.0 | 11.2 | 21.6 |
| 25 | $Hex_4NI$ | EPB | 0.4828 | 2.1266 | 1.8557 | 75.4 | 0.0 | 6.1 | 18.6 |
| 25 | $MeBu_3NI$ | EPB | 0.4601 | 1.7269 | 1.9164 | 67.9 | 0.0 | 13.7 | 18.4 |
| 25 | $Bu_3PhNI$ | EPB | 0.4021 | 1.8933 | 1.9682 | 77.1 | 0.0 | 7.5 | 15.5 |
| 25 | $Bu_4PBr$ | EPB | 0.4695 | 1.7703 | 1.9979 | 67.9 | 0.0 | 15.1 | 17.0 |
| 25 | $Et_4NI$ | EPB | 0.4130 | 1.7640 | 1.9970 | 94.9 | 0.0 | 5.1 | 0.0 |
| 25 | $Bu_4PI$ | EPB/DHF* | 0.4734 | 2.1924 | 2.5717 | 40.1 | 34.5 | 10.4 | 15.1 |
| 25 | $Bu_4NI$ | EPB/DHF* | 0.5197 | 2.1972 | 2.0026 | 34.6 | 31.7 | 15.6 | 18.1 |
| 25 | $Bu_4PBr$ | EPB/DHF* | 0.5054 | 2.0368 | 2.0942 | 35.3 | 30.7 | 21.2 | 12.7 |
| 25 | $Et_4NBr$ | EPB/DHF* | 0.4831 | 1.9026 | 1.9320 | 49.0 | 43.6 | 7.4 | 0.0 |
| 25 | $Bu_4PI$ | DHF | 0.4577 | 1.8567 | 2.0494 | 0.0 | 68.1 | 14.2 | 17.7 |
| 25 | $Bu_4NI$ | DHF | 0.4833 | 1.8670 | 1.9826 | 0.0 | 66.0 | 20.0 | 13.9 |
| 25 | $Et_4NBr$ | DHF | 0.4726 | 2.2443 | 2.3148 | 0.0 | 86.0 | 14.0 | 0.0 |
| 40 | $Bu_4PI$ | EPB | 0.4320 | 1.9198 | 2.1549 | 74.7 | 0.0 | 8.3 | 17.0 |
| 40 | $Bu_4NI$ | EPB | 0.5151 | 1.9733 | 2.1682 | 70.9 | 0.0 | 10.4 | 18.6 |
| 40 | $Bu_4PI$ | EPB/DHF* | 0.4910 | 1.9487 | 2.3293 | 36.6 | 31.6 | 13.7 | 18.1 |
| 40 | $Bu_4NI$ | EPB/DHF* | 0.4571 | 2.1402 | 1.9962 | 35.7 | 33.2 | 15.9 | 15.2 |
| 40 | $Bu_4PI$ | DHF | 0.4635 | 2.0480 | 2.1791 | 0.0 | 69.1 | 15.2 | 15.8 |
| 40 | $Bu_4Nt$ | DHF | 0.5146 | 2.1551 | 1.8511 | 0.0 | 65.8 | 20.7 | 13.5 |

TABLE 1-continued

| Temp. (°C.) | Catalyst | Organic Phase | EPB by diff. (wt %) | DHF by diff. (wt %) | Water (wt %) | Cat. (wt %) | Distrib. Coef. (org./aq.) Catalyst | Extraction Selectivity (cat./water) |
|---|---|---|---|---|---|---|---|---|
| 25 | $Me_4PI$ | EPB | 6.2 | 0.0 | 76.7 | 17.1 | 0.0 | 0.000 |
| 25 | $Me_3PhPI$ | EPB | 6.6 | 0.0 | 81.2 | 12.2 | 0.0 | 0.556 |
| 25 | $MePh_3Pt$ | EPB | 12.3 | 0.0 | 85.0 | 2.7 | 6.5 | 53.146 |
| 25 | $Bu_4PI$ | EPB | 10.5 | 0.0 | 87.0 | 2.5 | 8.2 | 88.330 |
| 25 | $Et_4NI$ | EPB | 19.0 | 0.0 | 64.8 | 16.2 | 0.0 | 0.075 |
| 25 | $Bu_4NI$ | EPB | 10.8 | 0.0 | 85.5 | 3.7 | 5.8 | 43.965 |
| 25 | $Hex_4NI$ | EPB | 5.0 | 0.0 | 94.6 | 0.5 | 40.1 | 623.812 |
| 25 | $MeBu_3NI$ | EPB | 11.4 | 0.0 | 84.1 | 4.5 | 4.1 | 25.149 |
| 25 | $Bu_3PhNI$ | EPB | 5.2 | 0.0 | 93.0 | 1.7 | 8.9 | 110.755 |
| 25 | $Bu_4PBr$ | EPB | 14.0 | 0.0 | 79.8 | 6.2 | 2.8 | 14.504 |
| 25 | $Et_4NI$ | EPB | 12.1 | 0.0 | 72.4 | 15.5 | 0.0 | 0.005 |
| 25 | $Bu_4PI$ | EPB/DHF* | 5.9 | 13.4 | 79.2 | 1.5 | 10.3 | 78.737 |
| 25 | $Bu_4NI$ | EPB/DHF* | 4.0 | 9.3 | 84.0 | 2.6 | 6.9 | 37.123 |
| 25 | $Bu_4PBr$ | EPB/DHF* | 4.4 | 9.6 | 78.4 | 7.5 | 1.7 | 6.289 |
| 25 | $Et_4NBr$ | EPB/DHF* | 4.0 | 8.9 | 69.3 | 17.8 | 0.0 | 0.006 |
| 25 | $Bu_4PI$ | DHF | 0.0 | 28.5 | 68.4 | 3.1 | 5.7 | 27.205 |
| 25 | $Bu_4NI$ | DHF | 0.0 | 35.0 | 59.8 | 5.2 | 2.7 | 8.002 |
| 25 | $Et_4NBr$ | DHF | 0.0 | 20.5 | 65.6 | 13.9 | 0.0 | 0.013 |
| 40 | $Bu_4PI$ | EPB | 15.7 | 0.0 | 82.5 | 1.8 | 9.5 | 94.818 |
| 40 | $Bu_4NI$ | EPB | 4.6 | 0.0 | 91.9 | 3.5 | 5.3 | 46.965 |
| 40 | $Bu_4PI$ | EPB/DHF* | 5.4 | 11.9 | 81.0 | 1.7 | 10.7 | 63.018 |
| 40 | $Bu_4NI$ | EPB/DHF* | 5.6 | 13.5 | 79.0 | 1.9 | 8.0 | 39.722 |
| 40 | $Bu_4PI$ | DHF | 0.0 | 32.9 | 64.9 | 2.2 | 7.2 | 30.924 |
| 40 | $Bu_4Nt$ | DHF | 0.0 | 33.3 | 61.8 | 4.8 | 2.8 | 8.343 |

Note: *EPB/DHF mixture was a 50:50 ratio, 20.17 g of EPB and 20.18 g DHF.

EXAMPLE 12

Determination of Distribution Coefficient of $MeBu_3NI$

Distribution coefficients typically depend on the solute concentration in the system. Therefore, the effect of solute concentration on the distribution coefficient of $MeBu_3NI$ was more fully investigated at 25° C.

In a first set of experiments, five glass vials were changed with two milliliters of water and two milliliters of EPB. Then 0.2, 0.4, 0.6, 0.8, and 5.0 grams of $MeBu_3NI$ were added to the first through fifth vials, respectively. The vials were vigorously agitated for five minutes to assure that solute transfer between the phases was complete. The contents of the vials were then decanted, and samples of the two liquid phases were taken and analyzed via gas chromatography. The contents of the fifth vial were a single liquid phase.

A second set of experiments was then performed to further quantify the effect of $MeBu_3NI$ concentration on the distribution coefficient. This time ten glass vials were charged with two milliliters of water and two milliliters of EPB. Then 1.0, 1.5, 2.0, 2.5, 3.0, 3.5, 4.0, 4.5, 5.0, 6.0 grams of $MeBu_3NI$ were added to the first through tenth vials, respectively. The vials were vigorously agitated for five minutes to assure that solute transfer between the phases was complete. The contents of the vials were then decanted, and samples of the two liquid phases were taken and analyzed via gas chromatography. All of the vials except the tenth one formed two immiscible phases. The contents of the tenth vial formed a single liquid phase. Therefore, the solute concentration was sufficiently high in that case to homogenize the ternary system. The phase volumes in the ninth vial were too small to sample, and the third and seventh samples were contaminated; therefore, the distribution coefficients for these runs are not reported. The distribution coefficients for the other experiments are summarized in Table 2.

TABLE 2

Phase equilibrium data for the $MeBu_3NI$, water, and EPB system at 25° C.

| Tie Line No. | Organic Phase | | | Aqueous Phase | | | Distribution Coefficient | Extraction |
|---|---|---|---|---|---|---|---|---|
| | EPB (wt %) | Water (wt %) | $MeBu_3NI$ (wt %) | EPB (wt %) | Water (wt %) | $MeBu_3NI$ (wt %) | $MeBu_3NI$ (org./aq.) | Selectivity (cat./water) |
| 1 | 73.22 | 21.38 | 5.39 | 5.47 | 91.31 | 3.22 | 1.67 | 7.15 |
| 2 | 79.48 | 6.32 | 14.20 | 4.00 | 91.96 | 4.00 | 3.55 | 51.65 |
| 3 | 71.36 | 7.60 | 21.04 | 4.36 | 90.75 | 4.88 | 4.31 | 51.48 |
| 4 | 64.73 | 8.87 | 26.40 | 4.73 | 90.18 | 5.09 | 5.19 | 52.73 |
| 5 | 58.82 | 10.73 | 30.45 | 5.01 | 86.99 | 8.00 | 3.81 | 30.86 |
| 6 | 44.75 | 14.33 | 40.92 | 5.52 | 85.81 | 8.67 | 4.72 | 28.26 |
| 7 | 31.76 | 17.41 | 50.84 | 6.54 | 77.50 | 15.96 | 3.19 | 14.18 |
| 8 | 26.08 | 19.61 | 54.32 | 4.26 | 82.77 | 12.96 | 4.19 | 17.69 |
| 9 | 23.16 | 20.78 | 56.06 | 2.91 | 82.81 | 14.28 | 3.93 | 15.64 |
| 10 | 20.09 | 22.32 | 57.59 | 3.57 | 79.19 | 17.24 | 3.34 | 11.85 |

EXAMPLE 13

Determination of Distribution Coefficients of 1,2- and 1,4-Butenediol

The distribution coefficients for 1,2- and 1,4-butenediol between water and EPB were measured at 25° C. in this experiment. Two milliliters of water and two milliliters of EPB were charged to a series of ten glass vials. Then, the following masses of a 50:50 mixture of 1,2- and 1,4-butenediol were added to each vial: 0.25; 0.50; 0.75; 1.00; 1.25; 1.50; 1.75; 2.00; 2.25; and 2.75. The vials were vigorously agitated for five minutes to ensure that solute transfer between the phases was complete. The contents of the vials were then decanted, and samples of the two liquid phases were taken and analyzed via gas chromatography. The distribution coefficients for these experiments are summarized in Table 3.

| Sample No. | Elapsed Time (minutes) | Fraction of MeBu$_3$NI Unextracted (weight) |
|---|---|---|
| 1 | 0 | No Sample |
| 2 | 19 | 0.055 |
| 3 | 71 | 0.069 |
| 4 | 90 | 0.062 |
| 5 | 102 | 0.072 |
| 6 | 121 | 0.073 |
| 7 | 138 | 0.083 |
| 8 | 187 | 0.076 |

While the invention has been described with reference to the Figures and the preferred embodiments, it is to be understood that variations and modifications may be resorted to as will be apparent to those skilled in the art. Such variations and modifications are to be considered

TABLE 3

Phase equilibrium data for the 1,2- and 1,4-butenediol, water, and EPB system at 25° C.

| Tie Line No. | Organic Phase | | | Aqueous Phase | | | Distribution Coefficient of Diols (organic/aqueous) | Extraction Selectivity (catalyst/water) |
|---|---|---|---|---|---|---|---|---|
| | EPB (wt %) | Water (wt %) | Diols (wt %) | EPB (wt %) | Water (wt %) | Diols (wt %) | | |
| 1 | 93.64 | 4.4 | 1.96 | 4.99 | 83.68 | 11.35 | 0.17 | 3.28 |
| 2 | 93.76 | 4.35 | 1.9 | 6.16 | 75.07 | 18.77 | 0.10 | 1.75 |
| 3 | 93.1 | 4.57 | 2.33 | 7.48 | 66.14 | 26.39 | 0.09 | 1.28 |
| 4 | 91.24 | 4.89 | 3.84 | 8.89 | 58.94 | 32.17 | 0.12 | 1.44 |
| 5 | 86.13 | 7.55 | 6.32 | 11.3 | 53.13 | 35.56 | 0.18 | 1.25 |
| 6 | 89.17 | 5.28 | 5.56 | 12.22 | 48.74 | 39.04 | 0.14 | 1.31 |
| 7 | 92.5 | 5.97 | 7.35 | 14.36 | 43.83 | 41.81 | 0.18 | 1.29 |

EXAMPLE 14

Countercurrent Extraction

A six-foot tall, one-half inch diameter, glass, reciprocating-plate, Karr extraction column was operated continuously in countercurrent mode for four hours to separate MeBu$_3$NI and iodobutenol catalysts from aqueous 1,4-diol and 1,2-diol formed by the hydrolysis of EPB. The Karr column consisted of: a five-foot tall active region where Teflon plates with a one-inch plate spacing and greater than 50% open area reciprocated; two six-inch tall by one-inch diameter expanded coalescing regions at the top and bottom of the extractor to minimize entrainment of the dispersed phase; and a complete jacket for temperature control. The feed was produced by the hydrolysis reaction of Example 3 and primarily consisted of EPB, water, MeBu$_3$NI, 1,2-butenediol, 1,4-butenediol, and 1,4-butanediol at 0.20, 56.2, 19.1, 1.5, 9.3, and 3.4 weight percents, respectively. The feed solution was pumped into the top of the active section of the extraction column at a rate of 14 mL/min.; and the solvent, consisting primarily of EPB, entered the extractor at the bottom of the active section at a rate of 14 mL/min. The reciprocation rate was initially 143 strokes per minute (spm) and was reduced to about 125 spm. The overall column flux was held constant at 325 gph/ft$^2$. Samples of the extract and raffinate were periodically collected and analyzed, and the results are summarized in the table below. The MeBu$_3$NI predominately distributed into the EPB phase while the butenediols and 1,4-butanediol preferentially distributed into the aqueous phase. The fraction of catalyst unextracted ranged between 0.055 and 0.129 during the course of the run.

within the purview and the scope of the claims appended hereto. For example, the use of hydrobromic acid and/or hydrochloric acid in place of all or part of the hydriodic acid, and the use of a chloride or bromide salt in place of all or part of the iodide salt are acceptable variations.

We claim:

1. A process for separating mixtures of 2-alkene-1,4-diols and 3-alkene-1,2-diols from an aqueous mixture comprising (A) an iodide salt, bromide salt, chloride salt, or mixtures thereof, (B) at least one of hydriodic acid, iodoalcohol, hydrobromic acid, bromoalcohol, hydrochloric acid, chloroalcohol, and precursors thereof, and (C) 2-alkene-1, 4-diols and 3-alkene-1,2-diols, said process comprising contacting said aqueous mixture with a γ,δ-epoxyalkene-containing organic extraction solvent at conditions effective to convert said hydriodic acid, hydrobromic acid, and hydrochloric acid, if present, to iodoalcohol, bromoalcohol, and chloroalcohol, respectively, and to form an aqueous phase comprising said 2-alkene-1,4-diols and 3-alkene-1,2-diols, and an organic phase comprising said iodoalcohol, bromoalcohol, or chloroalcohol, and said iodide salt, bromide salt, or chloride salt.

2. A process for separating mixtures of 2-alkene-1,4-diols and 3-alkene-1,2-diols from an aqueous mixture comprising (A) a bromide salt, (B) at least one of hydrobromic acid, bromoalcohol, and precursors thereof, and (C) 2-alkene-1, 4-diols and 3-alkene-1,2-diols, said process comprising contacting said aqueous mixture with a γ,δ-epoxyalkene-containing organic extraction solvent at conditions effective to convert said hydrobromic acid, if present, to bromoalcohol and to form an aqueous phase comprising said 2-alkene-1,4-diols and 3-alkene-1,2-diols, and an organic phase comprising said bromoalcohol and bromide salt.

3. A process for separating mixtures of 2-alkene-1,4-diols and 3-alkene-1,2-diols from an aqueous mixture comprising (A) an iodide salt, (B) at least one of HI, iodoalcohol, and precursors thereof, and (C) 2-alkene-1,4-diols and 3-alkene-1,2-diols, said process comprising contacting said aqueous mixture with a γ,δ-epoxyalkene-containing organic extraction solvent at conditions effective to convert said HI, if present, to iodoalcohol and to form an aqueous phase comprising said 2-alkene-1,4-diols and 3-alkene-1,2-diols, and an organic phase comprising said iodoalcohol and iodide salt.

4. The process according to claim 3, further comprising separating said organic phase from said aqueous phase.

5. The process according to claim 3, wherein said γ,δ-epoxyalkene is 3-methyl-3,4-epoxy-1-butene, 2-methyl-3,4-epoxy-1-butene, 2,3-dimethyl-3,4-epoxy-1-butene, or 3,4-epoxy-1-butene.

6. The process according to claim 3, wherein said γ,δ-epoxyalkene-containing organic extraction solvent comprises a co-extraction solvent selected from hydrocarbons, haloaromatics, ketones, esters, ethers, amides, and mixtures thereof.

7. The process according to claim 3, wherein said γ,δ-epoxyalkene-containing organic extraction solvent comprises a dense gas co-extraction solvent selected from carbon dioxide, methane, ethane, propane, butane, isobutane, dimethyl ether, fluorocarbons, and mixtures thereof.

8. The process according to claim 7, wherein said dense gas co-extraction solvent further comprises a cosolvent selected from acetone, tetrahydrofuran, 1,4-dioxane, acetonitrile, and mixtures thereof.

9. The process according to claim 3, wherein said iodide salt is a quaternary ammonium, phosphonium, or arsonium iodide.

10. The process according to claim 9, wherein said iodide salt is a tetraalkylammonium iodide.

11. The process according to claim 10, wherein said iodide salt is methyltributylammonium iodide.

12. A process for separating mixtures of 2-butene-1,4-diol and 3-butene-1,2-diol from an aqueous mixture comprising (A) an iodide salt, (2) at least one of HI, iodobutenol, and precursors thereof, and (C) 2-butene-1,4-diol and 3-butene-1,2-diol, said process comprising contacting said aqueous mixture with a 3,4-epoxy-1-butene-containing organic extraction solvent at conditions effective to convert said HI, if present, to iodobutenol and to form an aqueous phase comprising said 2-butene-1,4-diol and 3-butene-1,2-diol, and an organic phase comprising said iodobutenol and iodide salt.

13. The process according to claim 12, further comprising separating said organic phase from said aqueous phase.

14. The process according to claim 12, wherein said 3,4-epoxy-1-butene-containing organic extraction solvent comprises a co-extraction solvent selected from hydrocarbons, haloaromatics, ketones, esters, ethers, amides, and mixtures thereof.

15. The process according to claim 12, wherein said 3,4-epoxy-1-butene-containing organic extraction solvent comprises a dense gas co-extraction solvent selected from carbon dioxide, methane, ethane, propane, butane, isobutane, dimethyl ether, fluorocarbons, and mixtures thereof.

16. The process according to claim 15, wherein said dense gas co-extraction solvent further comprises a cosolvent selected from acetone, tetrahydrofuran, 1,4-dioxane, acetonitrile, and mixtures thereof.

17. The process according to claim 12, wherein said iodide salt is a quaternary ammonium, phosphonium, or arsonium iodide.

18. The process according to claim 17, wherein said iodide salt is a tetraalkylammonium iodide.

19. The process according to claim 18, wherein said iodide salt is methyltributylammonium iodide.

20. A process for separating mixtures of 2-alkene-1,4-diols and 3-alkene-1,2-diols from an aqueous mixture comprising (A) an HI salt of a sterically hindered pyridine and, optionally, an iodide salt, and (B) 2-alkene-1,4-diols and 3-alkene-1,2-diols, said process comprising contacting said aqueous mixture with an organic extraction solvent at conditions effective to form an aqueous phase comprising said 2-alkene-1,4-diols and 3-alkene-1,2-diols, and an organic phase comprising said HI salt and said iodide salt, if present.

21. The process according to claim 20, further comprising separating said organic phase from said aqueous phase.

22. The process according to claim 20, wherein said γ,δ-epoxyalkene is 3-methyl-3,4-epoxy-1-butene, 2-methyl-3,4-epoxy-1-butene, 2,3-dimethyl-3,4-epoxy-1-butene, or 3,4-epoxy-1-butene.

23. The process according to claim 20, wherein said sterically hindered pyridine is 2,6-dimethylpyridine, 2,4,6-trimethylpyridine, 2,6-di-tert-butylpyridine, 2,6-di-tert-butyl-4-methylpyridine, 2,4,6-tri-tert-butylpyridine, 2,6-diphenylpyridine, 2,4,6-triphenylpyridine, acridine, or 1,2,3,4,5,6,7,8-octahydroacridine.

24. The process according to claim 20, wherein said organic extraction solvent is selected from hydrocarbons, haloaromatics, ketones, esters, ethers, amides, and mixtures thereof.

25. The process according to claim 20, wherein said organic extraction solvent is a dense gas selected from carbon dioxide, methane, ethane, propane isobutane, isobutane, dimethyl ether, fluorocarbons, and mixtures thereof.

26. The process according to claim 25, wherein said dense gas further comprises a cosolvent selected from acetone, tetrahydrofuran, 1,4-dioxane, acetonitrile, and mixtures thereof.

* * * * *

UNITED STATES PATENT AND TRADEMARK OFFICE
CERTIFICATE OF CORRECTION

PATENT NO. : 5,856,591
DATED : January 5, 1999
INVENTOR(S) : Peter B. MacKenzie et al.

It is certified that error appears in the above-identified patent and that said Letters Patent is hereby corrected as shown below:

ON THE COVER PAGE:

After Item "[76] Inventors," the following should appear:

--[73] Assignee: Eastman Chemical Company, Kingsport, Tennessee.--.

In the "Attorney, Agent or Firm" section, "Burns, Doane, Swecker & Mathis, L.L.P." should not appear.

IN THE CLAIMS:

Column 19, line 41, "2" should appear as --B--.

Column 20, line 47, "isobutane" should appear as --butane--.

Signed and Sealed this

Twenty-second Day of August, 2000

*Attest:*

Q. TODD DICKINSON

*Attesting Officer*   *Director of Patents and Trademarks*